United States Patent [19]
Yang

[11] Patent Number: 5,407,943
[45] Date of Patent: Apr. 18, 1995

[54] AZASPIRO QUINOLONE ANTIBACTERIAL AGENTS

[75] Inventor: Bingwei V. Yang, Waterford, Conn.

[73] Assignee: Pfizer Inc., New York, N.Y.

[21] Appl. No.: 142,475

[22] PCT Filed: May 4, 1992

[86] PCT No.: PCT/US92/03453
§ 371 Date: Nov. 22, 1993
§ 102(e) Date: Nov. 22, 1993

[87] PCT Pub. No.: WO92/22550
PCT Pub. Date: Dec. 23, 1992

Related U.S. Application Data

[63] Continuation-in-part of Ser. No. 717,552, Jun. 19, 1991, abandoned.

[51] Int. Cl.$^6$ .............. C07D 401/04; A61K 31/47
[52] U.S. Cl. .................... 514/300; 514/312; 546/16; 544/6; 544/70
[58] Field of Search ............ 514/300, 312; 546/16

[56] References Cited

U.S. PATENT DOCUMENTS 4,571,396 2/1986 Hutt et al. ............... 546/94
5,245,037 9/1993 Kuramoto .............. 546/16

FOREIGN PATENT DOCUMENTS 0357047 3/1990 European Pat. Off.
1056673 3/1989 Japan.

*Primary Examiner*—Mark L. Berch
*Attorney, Agent, or Firm*—Peter C. Richardson; Paul H. Ginsburg; Gezina Holtrust

[57] ABSTRACT

Quinolone carboxylic acids of the formula

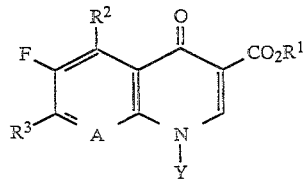

wherein $R^1$, $R^2$, A and Y are as defined herein, and $R^3$ is

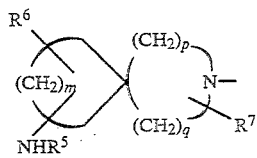

have antibacterial properties.

9 Claims, No Drawings

AZASPIRO QUINOLONE ANTIBACTERIAL AGENTS

This application is a 371 of PCT US92/3453, which is a CIP of 07/717,552 filed Jun. 19, 1991, abandoned.

The invention relates to novel 7-azaspiro substituted quinolone carboxylic acids, pharmaceutical compositions containing such compounds and methods of treatment with such compounds.

Since the introduction of the antibacterial agent nalidixic acid, 1,4-dihydro-1-ethyl-4-oxo-7-methyl-1,8-naphthyridine-3-carboxylic acid, in 1963, a large number of patents and scientific papers have been published on antibacterial compounds having a related naphthyridine or quinoline structure.

Representative of the most recent patent publications on the subject are European Patent Publication 357047, and Japanese Patent Publication 1056673. European Patent Publication 357047 refers to quinolines which are 7-substituted by an azaspiroalkyl group which in turn is amino-substituted in the azacycloalkyl group. Japanese Patent Publication 1056673 refers to quinolines which are 7-substituted by a pyrrolidinyl group which may have a spiro group attached thereto. The compounds of the invention instead are amino-substituted in a spiro group attached to a six-membered nitrogen-containing ring.

The invention provides antibacterial compounds having the formula

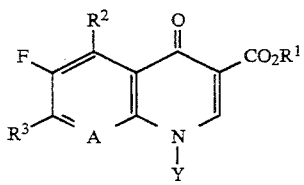

wherein $R^1$ is hydrogen, $C_1$-$C_3$ alkyl, benzyl, a pharmaceutically acceptable cation, or a prodrug group, A is CH, CF, CCl, COCH$_3$, C—CH=CH$_2$, C—($C_1$-$C_3$) alkyl, C—CF$_3$, C—CN or N; Y is $C_1$-$C_3$ alkyl, $C_1$-$C_2$ haloalkyl, cyclopropyl, halocyclopropyl, vinyl, 4-halophenyl, 2,4-difluorophenyl, methoxy or NHCH$_3$; or A and Y together form a group of the formula

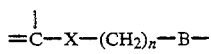

wherein X is O, S, or CH$_2$, n is 0 or 1, and B is CH—(C$_1$—C$_3$)alkyl, C=CH$_2$ or CH—CH$_2$F; $R^2$ is hydrogen, $C_1$-$C_4$ alkyl, $C_1$-$C_4$ alkoxy, amino, halogen or aminomethyl; and $R^3$ is a group of the formula

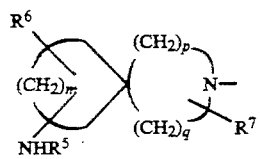

wherein $R^5$ is hydrogen, or $C_1$-$C_3$ alkyl, $R^6$ and $R^7$ are each independently hydrogen, $C_1$-$C_3$ alkyl or halogen, m is 2 or 3, p is 1 or 2, q is 2 or 3 and p+q is 4, and $R^6$ is located next to the group —NHR$^5$.

Preferred compounds of the invention are those of formula I wherein $R^1$ is hydrogen or a pharmaceutically acceptable cation such as sodium, and hydrates thereof.

Other preferred compounds are those wherein A is CH or N, those wherein Y is cyclopropyl or 2,4-difluorophenyl, and those wherein $R^2$ is hydrogen.

Preferred compounds are those wherein $R^3$ is 1-amino-6-azaspiro[2.5]oct-6-yl, 1-amino-5-azaspiro[2.5]oct-5-yl, or 2-amino-7-azaspiro[3.5]non-7-yl.

Specific preferred compounds of the invention are:

7-(1-amino-6-azaspiro[2.5]oct-6-yl)-1-cyclopropyl-6-fluoro-1,4-dihydro-4-oxo-quinoline-3-carboxylic acid, and 7-(2-amino-7-azaspiro[3.5]non-7-yl)-1-(2,4-difluorophenyl)-6-fluoro-1,4-dihydro-4-oxo-1,8-naphthyridine-3-carboxylic acid.

Specific compounds of the invention are:

7-(1-amino-6-azaspiro[2.5 ]oct-6-yl)-6-fluoro-1-(2,4-difluorophenyl)-1,4-dihydro-4-oxo-1,8-naphthyridine-3-carboxylic acid, 7-(1-amino-6-azaspiro[2.5 ]oct-6-yl)-1-cyclopropyl-6-fluoro-1,4-dihydro-4-oxo-1,8-naphthyridine-3-carboxylic acid, 7-(trans-1-amino-5-azaspiro[2.5]oct-5-yl)-1-cyclopropyl-6-fluoro-1,4-dihydro-4-oxo-1,8-naphthyridine-3-carboxylic acid, and 7-(cis-1-amino-5-azaspiro[2.5 ]oct-5-yl)-1-cyclopropyl-6-fluoro-1,4-dihydro-4-oxo-1,8-naphthyridine-3-carboxylic acid.

The invention includes a pharmaceutical composition comprising a pharmaceutically acceptable carrier or diluent and a compound of the formula I in an antibacterially effective amount.

The invention further includes a method of treating a host, such as an animal or a human being, having a bacterial infection comprising administering to the host an antibacterially effective amount of a compound of the formula I, or a pharmaceutical composition as defined above.

In one specific embodiment of the invention, when A and Y together are

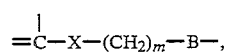

the compounds of formula I have the formula:

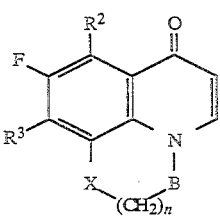

wherein X, $R^2$, $R^3$, B and n are as defined above with reference to formula I.

The compounds (I) of the invention may be prepared by reacting a compound of the formula

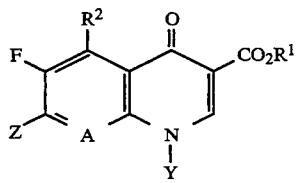

III wherein Z is a leaving group such as fluoro, chloro, bromo, $C_1$–$C_3$ alkylsulfonyl or phenylsulfonyl, and $R^1$, $R^2$, A and Y are as defined above in connection with formula I, with a compound of the formula $R^3H$ wherein $R^3$ is as defined above with reference to formula I, except that $R^5$ in the definition of $R^3$ does not include hydrogen, but is $C_1$–$C_3$ alkyl or the N-protecting group $R^5$. Nitrogen protecting groups $R^8$ are known in the art, and include $C_1$–$C_6$ acyl, $C_2$–$C_6$ alkoxycarbonyl such as t-butoxycarbonyl (t-BOC), optionally substituted benzyloxycarbonyl, aryloxycarbonyl, silyl, trityl, tetrahydropyranyl, vinyloxycarbonyl, O-nitrophenylsulfonyl, diphenylphosphinyl, p-toluenesulfonyl, and benzyl. The nitrogen protecting group is removed by methods known in the art such as hydrogenation or hydrolysis to form compounds of formula I wherein $R^5$ is hydrogen. Conveniently, when $R^8$ is a hydrolyzable nitrogen protecting group such as t-BOC and $R^1$ is $C_1$–$C_3$ alkyl or benzyl, removal of $R^8$ and $R^1$ is attained in one step by acid hydrolysis.

The reaction may be conducted with or without a solvent. The solvent, when used, must be inert under the reaction conditions. Suitable solvents are acetonitrile, tetrahydrofuran, ethanol, chloroform, dimethylsulfoxide, dimethylformamide, pyridine, water, or mixtures thereof.

The reaction temperature usually ranges from about 20° C. or about 150° C.

The reaction may advantageously be carried out in the presence of an acid acceptor such as an inorganic or organic base, e.g. an alkali metal or alkaline earth metal carbonate or bicarbonate, or a tertiary amine, e.g. triethylamine, pyridine or picoline.

When $R^1$ is $C_1$–$C_3$ alkyl, conversion to the corresponding acid may be carried out under acidic or basic conditions conventional for hydrolysis of carboxylic acid ester, at about 20° to 150° C.

The starting materials of formula III are known in the art, e.g. as disclosed in U.S. Pat. Nos. 4,571,396 and 4,775,668, the disclosures of which are herewith incorporated by reference.

The starting material of formula $R^3H$ has the following general formula

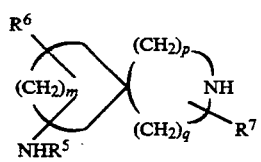

wherein $R^5$, $R^6$ and $R^7$, m, p and q are as defined above in connection with formula I. The specific formulas of such starting materials are as follows:

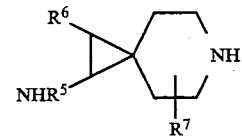

V

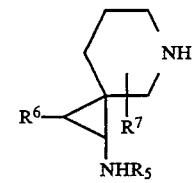

VI

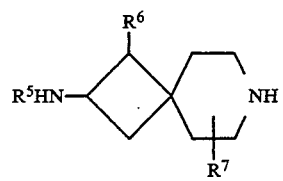

VII

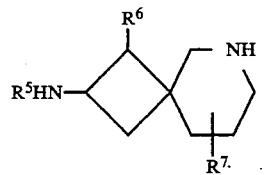

VIII

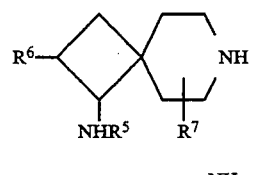

IX

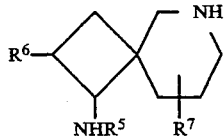

X

The preparation of compounds V to X is outlined below in sections which refer to the formula of the compounds prepared.

Since the starting materials V to X may have one or more asymmetric carbon atoms, the process of their preparation may result in a mixture of isomers, such as diastereoisomers and enantiomers. The compounds of formula I when resulting from reaction of these isomers will be isomeric as well. The invention includes all of the isomers of the compounds of formula I whether in mixtures, as isolated diastereomers or enantiomers. Any separation into diastereoisomers and enantiomers can be carried out by conventional methods.

In the processes described below, when reference is made to protection of the nitrogen in the piperidine ring, this is conveniently attained by reaction with benzylchloroformate and sodium carbonate to form a benzyloxycarbonyl (CBZ) group at the nitrogen of the piperidine ring (hereafter N-CBZ-protected).

Removal of the protecting group at the nitrogen of the piperidine (hereafter deprotection of the piperidine) may be attained by hydrogenolysis to remove the CBZ group. The hydrogenolysis is generally conducted in a reaction inert solvent such as a $C_1$–$C_6$ alcohol, or an aromatic or ethereal solvent such as benzene or tetrahydrofuran, in the presence of a catalyst. Suitable catalysts are nobel metals such as palladium, platinum and rhodium, and Raney nickel. The usual reaction times are from about 3 to 12 hours. The reaction is suitably conducted in ethanol in the presence of ammonium formate and palladium on activated carbon at room temperature.

$R^6$ and $R^7$-substituted-1-($R^5$-substituted-amino)-6-azaspiro[2.5]octane (V)

(a) $R^6$ is hydrogen or $C_1$–$C_3$ alkyl.

Referring to scheme 1, N-CBZ-protected $R_7$-substituted-4-piperidone of formula 1 is reacted with a Wittig reagent prepared from triphenylphosphine and a ($C_1$–$C_3$) alkylhalide such as a ($C_1$–$C_3$) alkyl bromide or iodide in the presence of a base. Suitable bases include methylsulphinyl carbanion ($CH_3SOCH_2^-$, generated from dimethyl sulfoxide with sodium hydride), sodium hydride, potassium t-butoxide, alkali hexamethyldisilazide, lithium diisopropylamide (LDA), n-butyl lithium or phenyl lithium. The reaction is conducted in a polar aprotic solvent, such as dimethylsulfoxide, dimethylformamide, tetrahydrofuran, ethyl ether or a $C_1$–$C_6$ alcohol such as ethanol. The reaction temperature generally ranges from about −100° C. to about 100° C. and the reaction time ranges from about 10 minutes to about 12 hours. Preferably, the conversion of 1 to 2 is carried out in the presence of sodium hydride in dimethyl sulfoxide at about 55° C. for about 3 hours. Alternatively, compounds of the formula 1 may be converted to compounds of the formula 2 by Peterson olefination. This reaction is usually conducted with trimethylsilylmethylmagnesium chloride in tetrahydrofuran at −78° C. followed by conversion of the product formed to a compound of the formula 2 in the presence of sodium hydride or sodium hydroxide.

such as toluene, benzene or hexane, or halogenated hydrocarbons. The reaction temperature generally ranges from room temperature to the reflux temperature of the solvent, and the reaction time from about 10 minutes to about 24 hours. Preferably, the reagent is ethyl diazoacetate, the catalyst is rhodium acetate, the solvent is methylene chloride, and the reaction temperature is room temperature.

The compound of formula 3 is converted to the corresponding acid, wherein $R_1'$ is hydrogen, by reaction with aqueous alkali hydroxide in the presence of a co-solvent such as dioxane, alcohol or tetrahydrofuran at a reaction temperature of from about room temperature to the reflux temperature of the solvent.

The acid is converted to a compound of the formula 4 by formation of an activated intermediate such as an acid chloride or a mixed anhydride, followed by reaction with an alkali metal azide in a solvent mixture of water and a co-solvent, such as acetone or tetrahydrofuran. The rearrangement of the resulting acyl azide is carried out in refluxing hydrocarbon solvent such as toluene in the presence of t-butanol and an organic acid catalyst such as p-toluenesulfonic acid or 4-tert-butylcatechol. The preferred reagents for the formation of acyl azide are ethyl chloroformate and sodium azide.

The compounds of formula 4 are hydrolyzed in the presence of an acid to form the compounds of formula 5 wherein $R^5$ is hydrogen. Suitable acids include mineral acids such as hydrochloric acid, and other strong acids such as trifluoroacetic acid.

The compounds of formula 5 wherein $R_5$ is $C_1$–$C_3$ alkyl are obtained from the compounds of formula 5 wherein $R_5$ is hydrogen by alkylation with an alkyl aldehyde of the formula R'CHO wherein R' is $C_1$–$C_3$ alkyl and subsequent reduction with a metal hydride.

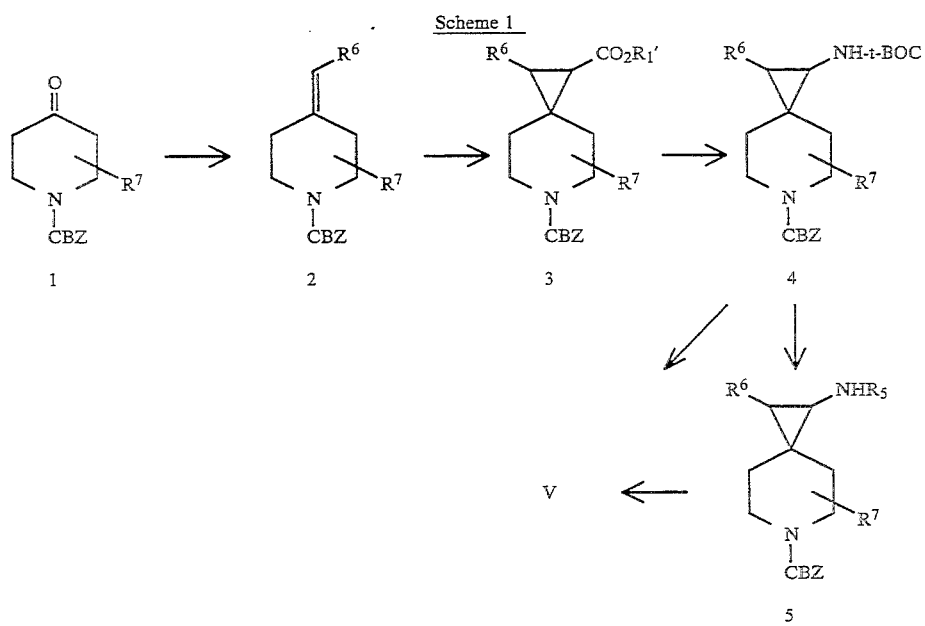

Scheme 1

The compounds of formula 2 are converted to compounds of the formula 3 wherein $R_1'$ is ($C_1$–$C_6$) alkyl by reaction with an alkyldiazoester in the presence of an inorganic salt. Suitable inorganic salts are copper salts such as cupric sulfate, rhodium salts such as rhodium acetate, or palladium salts such as palladium acetate, or copper bronze. Suitable solvents are ethereal solvents such as ether or tetrahydrofuran, and hydrocarbons The alkylation is generally carried out in a reaction inert solvent such as a hydrocarbon, a halogenated hydrocarbon, an aromatic solvent or an ethereal solvent in the presence of a catalyst, at a temperature from about 15° C. to the reflux temperature of the solvent. Suitable solvents include hexane, benzene, toluene, chloroform, methylene chloride, THF, ether and ethyl acetate. The reaction temperature is preferably maintained between room temperature and the reflux temperature of the solvent. The catalyst may be an organic acid, a mineral acid, a polymer supported acid, a metal halide or molecular sieves. Examples of appropriate catalysts are titanium trichloride, titanium tetrachloride, camphor sulfonic acid and hydrogen chloride. Suitable metal hydrides are sodium cyanoborohydride, potassium cyanoborohydride, sodium borohydride and borane.

Deprotection of the piperidine in the compounds of formula 4 or 5 results in compounds of the formula V wherein $R^5$ is a t-BOC group or $C_1$–$C_3$ alkyl.

(b) $R^6$ is halogen.

Scheme 2

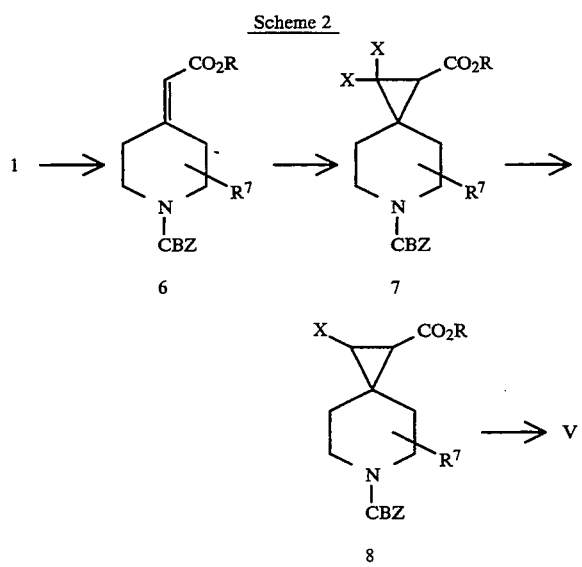

Referring to scheme 2, the compound of formula 1 (see scheme 1) is converted to a compound of the formula 6 by reaction with Horner-Emmons reagent which is prepared by reacting triethyl or other $C_1$–$C_3$ alkyl phosphite with a halide of the formula $R_1'CO_2CH_2X$ wherein $R_1'$ is $C_1$–$C_3$ alkyl and X is a halogen including chloro and bromo. The reaction is conducted in the presence of a base such as sodium hydride, potassium t-butoxide, alkali hexamethyldisilazide wherein the alkali is lithium, sodium or potassium, lithium diisopropylamide, n-butyl lithium, and phenyl lithium. The reaction solvent is suitably a polar aprotic solvent including dimethylsulfoxide, dimethylformamide, tetrahydrofuran, ethyl ether or a $C_1$–$C_6$ alcohol, e.g. ethanol. The reaction temperature generally ranges from about $-100°$ C. to about $100°$ C. and the reaction time ranges from about 10 minutes to about 12 hours. Usually, the conversion of compound 1 to compound 6 is carried outin the presence of sodium hydride in tetrahydrofuran at 70° C. for 3 hours.

The compounds of the formula 6 are converted into compounds of the formula 7 wherein X is halogen such as chloro or bromo by reaction with chloroform or bromoform in the presence of a base such as potassium t-butoxide, and alkali hydroxide, in the optional presence of a phase transfer catalyst such as a quaternary ammonium or phosphonium salt, for instance, triethylbenzylammonium chloride or tributylhexadecylphosphonium bromide. Suitable solvents are an ethereal solvent such as ethyl ether, a halogenated hydrocarbon such as chloroform or methylene chloride, or a hydrocarbon such as toluene, benzene or hexane. When a phase transfer catalyst is present, water is used as a co-solvent.

The monodehalogenation of the compound of formula 7 to form the compound of formula 8 is generally attained by partial reduction with a metal hydride such as lithium aluminum hydride or sodium borohydride in the presence of a catalyst such as tributyltin chloride, sodium borohydride in the optional presence of 2,2'-azabis(isobutyronitrile), or low valent metals such as zinc, lithium or sodium. Suitable solvents are benzene, hexane, tetrahydrofuran or a $C_1$–$C_6$ alcohol. Reaction temperatures range from about $-140°$ C. to about the reflux temperature of the reaction solvent. Reaction times range from about 10 minutes to about 24 hours.

The above dehalogenation may result in the reduction of the ester of formula 7 to produce a compound of the formula 8 having an alcohol group rather than an ester group. In that case, an additional step is required to convert the alcohol to the corresponding ester by conventional oxidation.

The compound of the formula V wherein $R^6$ is halogen is prepared from a compound of the formula 8 in the same manner as described above for the preparation of a compound of the formula V from a compound of formula 3 with reference to Scheme 1.

$R^6$ and $R^7$-substituted-1-($R^5$-substituted-amino)-5-azaspiro[2.5]octane (VI)

(a) $R^6$ is hydrogen or $C_1$–$C_3$ alkyl.

The preparation of the compounds of formula VI proceeds as described with reference to Scheme 1 using as the starting material a compound of the formula

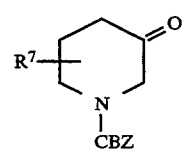

instead of the compound of formula 1.

(b) $R^6$ is halogen.

The preparation of the compounds of formula VI wherein $R^6$ is halogen proceeds as described with reference to Scheme 2 again using as the starting material a compound of the formula 9 instead of a compound of the formula 1.

$R^7$-substituted-1-($R^6$-substituted)-2-($R^5$-substituted-amino)-7-azaspiro[3.5]nonane (VII)

Referring to scheme 3, a compound of the formula 1 (see Scheme 1) is reacted with a Wittig reagent prepared from triphenylphosphine and methyl bromide or methyl iodide, as described with reference to Scheme 1 in the preparation of a compound of the formula 2, to prepare a compound of the formula 10.

Scheme 3

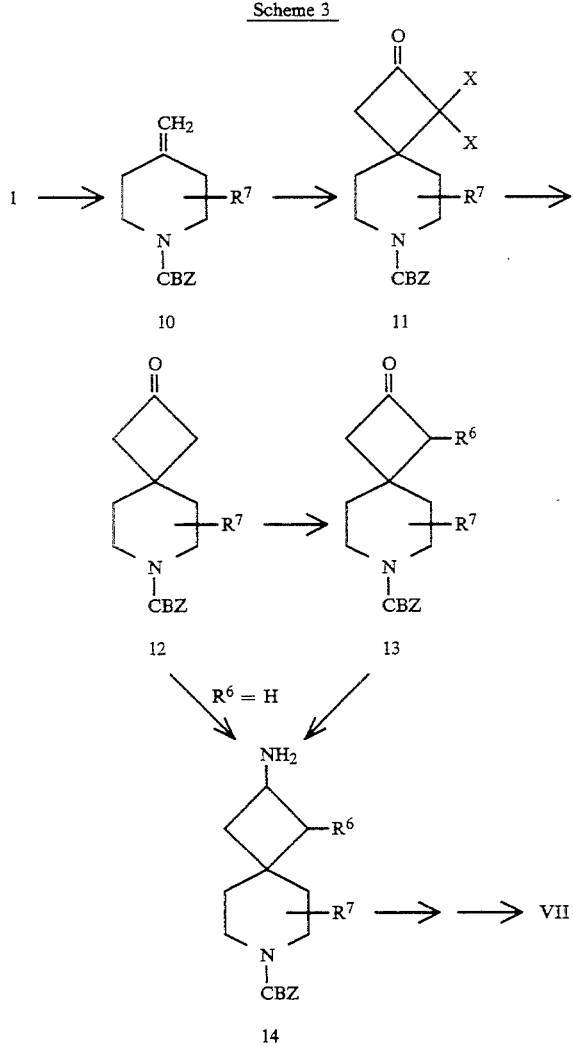

The compound of the formula 11 wherein X is halogen such as chloro or bromo is obtained by reacting a compound of the formula 10 with dichloroketene prepared from trichloroacetyl halide, such as the chloride and bromide, with activated zinc or from dichloroacetyl halide, such as the chloride and bromide, with a trialkyl amine such as triethylamine. Suitable solvents are tetrahydrofuran, ethyl ether or hexane. Preferably, the reaction is carried out with trichloroacetyl chloride, zinc-copper couple, and phosphorus oxychloride in anhydrous ether at reflux for 3 to 12 hours.

Dehalogenation of the compound of the formula 11 yields the compound of the formula 12. The reaction is generally conducted in the presence of activated zinc in an acidic medium such as acetic acid or ammonium chloride in a $C_1$–$C_6$ alcohol such as methanol. The reaction is conveniently carried out at about the reflux temperature of the solvent for about twelve hours.

The compounds of the formula 12 are α-alkylated or α-halogenated to form compounds of the formula 13 wherein $R_6$ is $C_1$–$C_3$ alkyl or halogen. The α-alkylation is generally conducted with a $C_1$–$C_6$ alkyl halide such as a bromide or chloride in the presence of a base in a polar aprotic solvent. Suitable bases are sodium hydride, potassium t-butoxide, alkali hexamethyldisilazide, lithium diisopropylamide, alkali hydroxide or alkali carbonate. Suitable solvents are dimethylsulfoxide, dimethylformamide, tetrahydrofuran, a halohydrocarbon or a $C_1$–$C_6$ alcohol. The reaction temperature ranges from about −100° C. to about the reflux temperature of the solvent. The reaction time ranges from about 10 minutes to about twelve hours.

The α-halogenation is generally carried out with chlorine or bromine in the presence of a Lewis acid such as aluminum chloride or bromide in a solvent such as a halogenated hydrocarbon or an aromatic hydrocarbon at a temperature of from about 0° C. to about room temperature.

The carbonyl group in the compounds of the formula 12 or 13 may be converted into an amino group by three different methods. In one method, the carbonyl group is reacted with methyl hydroxylamine in the presence of a base such as an alkali hydroxide, alkali carbonate or an amine such as triethylamine in a mixture of water and a co-solvent such as a $C_1$–$C_6$ alcohol, dioxane or tetrahydrofuran. The formed O-methyloxime is reduced to the corresponding amine (14) with a metal hydride such as borane, sodium borohydride, or by way of a dissolving metal reduction such as sodium in ethanol.

In another method, the carbonyl group is converted to the amino group by reaction with ammonium acetate in the presence of a reducing agent such as a metal hydride e.g. sodium cyanoborohydride, in an ethereal solvent or a $C_1$–$C_6$ alcohol, e.g. methanol, at a temperature of about 0° C. to about the reflux temperature of the solvent.

In yet another method, the amino compound (14) is formed through a series of intermediate steps wherein the carbonyl is first converted into hydroxy by reduction with a metal hydride such as lithium aluminum hydride, an alkali borohydride, or borane, in a solvent such as ether, tetrahydrofuran or a $C_1$–$C_6$ alcohol, e.g. methanol, at a temperature from about 0° C. to about room temperature. The alcohol is converted into the corresponding mesylate or tosylate by reaction with methanesulfonyl chloride or p-toluenesulfonyl chloride in the presence of a base such as triethylamine, 4-dimethylaminopyridine or pyridine, in a solvent such as a halogenated hydrocarbon at about 0° C. to about room temperature. The mesylate or tosylate is converted into the corresponding azide by reaction with an alkali metal azide, such as lithium or sodium azide, in a polar aprotic solvent such as exemplified before, e.g. acetonitrile or dimethyl formamide, at about room temperature to about the reflux temperature of the solvent.

The azide is reduced with a metal hydride such as sodium borohydride, lithium aluminumhydride or tributyltinhydride in a solvent such as ethyl ether, tetrahydrofuran, or a $C_1$–$C_6$ alcohol, or with triphenylphosphine followed by hydrolysis, or by hydrogenation in the presence of a noble metal such as palladium or rhodium. The hydrogenolysis is most conveniently carried out in the presence of Lindlar's catalyst in methanol under one atmosphere of hydrogen.

The compounds of the formula 14 are reacted with di-t-butyl carbonate in the presence of a base such as alkali hydroxide or triethyl amine in a mixture of water and a co-solvent such as tetrahydrofuran, dioxane or acetone, to obtain corresponding compounds wherein one hydrogen of the amino group is replaced by the t-butoxy carbonyl (t-BOC) group. The compound of formula VII wherein $R^5$ is t-BOC is then formed by deprotection of the piperidine in a manner similar to that described for the preparation of compound V from the compound 4 in scheme 1.

The compounds of the formula 12 or 13 may be formed into corresponding compounds wherein the carbonyl group is replaced by an aminoalkyl group by reaction with a compound of formula $R^5NH_2$ wherein $R^5$ is $C_1$-$C_3$ alkyl in the presence of a reducing agent such as a metal hydride, such as sodium cyanoborohydride, in an ethereal solvent or a $C_1$-$C_6$ alcohol, such as methanol, at about 0° C. to about the reflux temperature of the solvent. The corresponding compound of formula VII wherein $R^5$ is $C_1$-$C_3$ alkyl is then formed similarly to the method for preparing compound V from compound 5 in scheme 1 by deprotection of the piperidine.

$R^7$-substituted-1-($R^6$-substituted)-2-($R^5$-substituted-amino)-6-azaspiro[3.5]nonane (VIII)

The compounds of the formula VIII are prepared from compounds of the formula 9 in a manner similar to that described for the preparation of compounds of the formula VII from compounds of the formula 1 in scheme 4.

$R^7$-substituted-2-(R6-substituted)-1-($R^5$-substituted-amino)-7-azaspiro[3.5]nonane (IX)

Referring to scheme 4, the compounds of the formula 1 (see Scheme 1) are converted into the compounds of the formula 17 by reaction with diphenylsulfonium cyclopropylide formed from cyclopropylsulfonium fluoroborate and a base such as potassium hydroxide or potassium t-butoxide in dimethylsulfoxide at about room temperature, followed by treatment of the formed compounds of the formula 15 with a strong acid such as tetrafluoroboric acid or hydrochloric acid.

Alternatively, the compounds of the formula 1 may be reacted with the lithiated anion of cyclopropyl phenyl sulfide formed from n-butyllithium and cyclopropyl phenyl sulfide in tetrahydrofuran at about 0° C., followed by treating the intermediate compounds of the formula 16 with a catalytic amount of a Lewis acid such as fluoroboric acid, p-toluenesulfonic acid or stannic chloride to yield the compounds of the formula 17.

Scheme 4

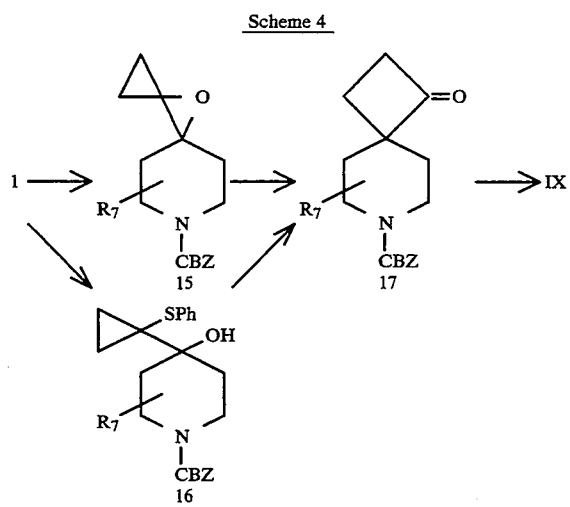

The compounds of the formula 17 are further reacted in a manner similar to that described in Scheme 3 for the preparation of the compounds of the formula VII from compounds of the formula 12 to yield the compounds of the formula IX.

$R^7$-substituted-1-($R^5$-substituted-amimo)-2-($R^6$-substituted)-6-azaspiro[3.5]nonane (X)

The compounds of the formula X are prepared from the compounds of the above formula 9 in a manner similar to that described for the preparation of the compounds of the formula IX from the compounds of the formula 1 (see Scheme 1).

The pharmaceutically acceptable cationic salts of compounds (I) may be prepared by conventional methods from the corresponding acids, e.g. by reaction with about one equimolar amount of a base. These cationic salts do not increase the toxicity of the compound toward animal organisms. Examples of suitable cationic salts are those of alkali metals such as sodium or potassium, alkaline earth metals such as magnesium or calcium, and ammonium or organic amines such as diethanoi amine or N-methylglucamine.

The novel compounds of formula I are useful in the treatment of bacterial infections of broad spectrum, particularly the treatment of gram-positive bacterial strains.

The compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5-5000 ppm, preferably 25-500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1–50 mg/kg/day, advantageously 0.2–10 mg/kg/day given in a single daily dose or up to 3 divided doses.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5-50 mg/kg/day given in a single dose or up to 3 divided doses. For intramuscular or intravenous administration, dosage levels are about 0.1-200 mg/kg/day, advantageously 0.5-50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the invention.

EXAMPLE 1

A.
7-(1-tert-Butoxycarbonylamino-6-azaspiro[2.5]oct-6-yl)-6-fluoro-1-(2,4-difluorophenyl)-1,4-dihydro-4-oxo-1,8-naphthyridine-3-carbOxylic acid, ethyl ester A solution of 1-tert-butoxycarbonylamino-6-azaspiro[2.5]octane (250 mg, 1.11 mmol), the ethyl ester of 7-chloro-6-fluoro-1-(2,4-difluorophenyl)-1,4-dihydro-4-oxo-1,8-naphthyridine-3-carboxylic acid (382 mg, 1.00 mmol) and triethylamine (0.78 ml, 5.55 mmol) in acetonitrile (15 ml) was heated at reflux overnight. Solvent was removed in vacuo and the residue was chromatographed on silica gel (eluents: 50% ethyl acetate/hexane, then 5:5:1 ethyl acetate/hexane/methanol) to afford the title product as an off-white solid (494 mg, 0.86 mmol, yield 86%).

$^1$H NMR (CDCl$_3$): 8.36 (s, 1H), 8.05 (d, J=13.5 Hz, 1H), 7.39 (m, 1H), 7.01 (m, 2H), 4.70 (bs, 1H), 4,35 (q, J=7.2 Hz, 2H), 3.52 (bm, 2H), 3.58 (bm, 4H), 2.41 (m, 1H), 1.46 (bm, 4H), 1.40 (s, 9H), 1.36 (t, J=7.2 Hz, 3H), 0.71 (m, 1H), 0.31 (t, J=4.5 Hz, 1H).

B.
7-(1-Amino-6-azaspiro[2.5]oct-6-yl)-6-fluoro-1-(2,4-difluorophenyl)-1,4-dihydro-4-oxo-1,8-naphthyridine-3-carboxylic acid, hydrochloride salt A solution of the compound of step A (441 mg, 0.77 mmol) in ethyl acetate (9 ml) and 3N hydrogen chloride (9 ml) was heated to reflux overnight. solvents were removed in vacuo and the residue was recrystallized from methanolacetonitrile to give the title product as a yellow solid, mp 217° C. (decomap.), (133 mg, 0.29 mmol, 38% yield).

$^1$H NMR (DMSO-d$_6$): 8.80 (s, 1H), 8.04 (d, J=13.4 Hz, 1H), 7.70 (m, 1H), 7.32 (m, 1H), 7.24 (m, 1H), 3.90 (bm, 2H), 3.53 (bm, 2H), 2.55 (m, 1H), 1.77 (m, 1H), 1.59 (bm, 2H), 1.31 (m, 1H), 1.01 (m, 1H), 0.81 (t, J=4.7, 1H).

EXAMPLE 2

A.
7-(1-tert-Butoxycarbonylamino-6-azaspiro[2.5]oct-6-yl)-1-cyclopropyl-6-fluoro-1,4-dihydro-4-oxo-quinoline-3-carboxylic acid According to the procedure of example 1A, 1-tert-butoxycarbonylamino-6-azaspiro[2.5]octane (260.0 mg, 1.15 mmol ) and 1-cyclopropyl-6,7-difluoro-1,4-dihydro-4-oxo-quinoline-3-carboxylic acid (274 mg, 1.04 mmol) were reacted to generate the title product (472 mg, 1.00 mg, 97% yield).

$^1$H NMR (CDCl$_3$): 8.71 (s, 1H), 7.93 (d, J=13.2 Hz, 1H), 7.34 (d, J=7.3 Hz, 1H), 4.70 (bs, 1H), 3.51-3.37 (bm, 5H), 2.50 (bm, 1H), 1.73 (bm, 2H), 1.50 (bm, 2H), 1.42 (s, 9H), 1.33 (d, J-7.3 Hz, 2H), 1.17 (m, 2H), 0.80 (m, 1H), 0.40 (t, J=4.6 Hz, 1H).

B.
7-(1-Amino-6-azaspiro[2.5]oct-6-yl)-1-cyclopropyl-6-fluoro-1,4-dihydro-4-oxo-quinoline-3-carboxylic acid, hydrochloride salt According to the procedure of example 1B, the compound of step A (420 mg, 0.89 mmol) was hydrolyzed with hydrochloric acid to provide the title product, mp 218° C. (decomp.), 197 mg (0.53 mmol, 60% yield).

$^1$H NMR (DMSO-d$_6$): 8.65 (bs, 3H), 7.87 (d, J=13.3 Hz, 1H), 7.59 (d, J=7.5 Hz, 1H), 3.85 (m, 2H), 3.64 (m, 1H), 3.44 (m, 1H), 3.29 (m, 2H), 1.95 (m, 1H), 1.88 (m, 1H), 1.65 (m, 1H), 1.51 (m, 1H), 1.31 (m, 2H), 1.23 (m, 2H), 0.87 (d, J=5.9 Hz, 1H).

EXAMPLE 3

A.
7-(1-tert-Butoxycarboxylamino-6-azaspiro[2.5]oct-6-yl)-1-cyclopropyl-6-fluoro-1,4-dihydro-4-oxo-1,8-naphthyridine-3-carboxylic acid, ethyl ester According to the procedure of example 1A, 1-tert-butoxycarbonylamino-6-azaspiro[2.5]octane (170 mg, 0.75 mmol) and the ethyl ester of 7-chloro-1-cyclopropyl-6-fluoro-1,4-dihydro-4-oxo-1,8-naphthyridine-3-carboxylic acid (229 mg, 0.74 mmol) were reacted to generate the title product (348 mg, 0.70 mmol, 94% yield).

$^1$H NMR (CDCl$_3$): 8.43 (s, 1H), 8.01 (d, J=13.5 Hz, 1H), 4.77 (bs, 1H), 4.32 (q, J=7.3 Hz, 2H), 3.86 (m, 4H), 3.44 (m, 1H), 2.46 (m, 1H), 1.61 (m, 2H), 1.56 (m, 1H), 1.40 (s, 9H), 1.34 (t, J=7.3 Hz, 3H), 1.26 (m, 1H), 1.13 (d, J=7.3 Hz, 2H), 0.97 (m, 2H), 0.75 (m, 1H), 0.37 (t, J=4.7 Hz, 1H).

B.
7-(1-Amino-6-azaspiro[2.5]oct-6-yl)-1-cyclopropyl-6-fluoro-1,4-dihydro-4-oxo-1,8-naphthyridine-3-carboxylic acid, hydrochloride salt According to the procedure of example 1B, the compound of step A (331 mg, 0.66 mmol) was hydrolyzed with hydrochloric acid to provide the title product, mp 217°-220° C. (decomp.) (135 mg, 0.33 mmol, 50% yield).

$^1$H NMR (DMSO-d$_6$): 8.59 (s, 1H), 8.54 (bs, 2H), 8.05 (d, J=14.0 Hz, 1H), 4.12 (m, 1H), 3.93 (m, 1H), 3.85 (m, 2H),\3.70 (m, 1H), 2.48 (m, 1H), 1.85 (m, 1H), 1.80 (m, 1H), 1.55 (m, 1H), 1.49 (m, 1H), 1.15 (m, 2H), 1.10 (m, 2H), 0.85 (m, 2H).

EXAMPLE 4

A. 7-(trans-1-tert-Butoxycarbonylamino-5-azaspiro[2.5]oct-5-yl)-1-cyclopropyl-6-fluoro-1,4-dihydro-4-oxo-1,8-naphthyridine-3-carboxylic acid, ethyl ester According to the procedure of example 1A, trans-1-tert-butoxycarbonylamino-5-azaspiro[2.5 ]octane, hydrochloride (125 mg. 0.47 mmol) and the ethyl ester of 7-chloro-1-cyclopropyl-6-fluoro-1,4-dihydro-4-oxo-1,8-naphthyridine-3-carboxylic acid (147 mg, 0.47 mmol) were reacted to generate the title product (240 mg, 0.47 mmol, 100% yield).

$^1$H NMR (CDCl$_3$): 8.41 (s, 1H), 7.96 (d, J=13.8 Hz, 1H), 4.73 (bs, 1H), 4.30 (q, J=7.3 Hz, 2H), 4.05 (m, 1H), 3.55 (m, 2H), 3.40 (m, 2H) 2.52 (m, 1H), 1.76 (m, 3H), 1.52 (m, 1H), 1.33 (br s, 9H), 1.30 (s, 3H), 1.11 (d, J=7.3 Hz, 2H), 0.94 (m, 2H), 0.86 (m, 1H), 0.34 (br s, 1H).

B.
7-(trans-1-Amino-5-azaspiro[2.5]oct-5-yl)-1-cyclopropyl-6-fluoro-1,4-dihydro-4-oxo-1,8-naphthyridine-3-carboxylic acid, hydrochloride salt According to the procedure of example 1B, the product of step A (235 mg, 0.47 mmol) was hydrolyzed with hydrochloric acid to provide the title product, mp 210°-215° C. (decomp.) (72.0 mg, 0.18 mmol, 38% yield).

$^1$H NMR (DMSO-d$_6$): 8.59 (s, 1H), 8.46 (bs, 2H), 8.04 (d, J=13.9 Hz, 1H), 3.93 (m, 2H), 3.68 (m, 3H), 2.63 (m, 1H), 1.86 (m, 3H), 1.83 (m, 1H), 1.18 (d, J=7.2 Hz, 2H), 1.10 (m, 2H), 1.09 (t, J=7.2 Hz, 1H), 0.76 (t, J=4.0 Hz, 1H).

EXAMPLE 5

A.
7-(2-tert-Butoxycarbonylamino-7-azaspiro[3.5]non-7-yl)-6-fluoro-1-(2,4-difluorophenyl)-1,4-dihydro-4-oxo-1,8-naphthyridine-3-carboxylic acid, ethyl ester A solution of 2-tert-butoxycarbonylamino-7-azaspiro[3.5]nonane (200 mg, 0.83 mmol) and the ethyl ester of 7-chloro-6-fluoro-1-(2,4-difluorophenyl)-1,4-dihydro-4-oxo-1,8-naphthyridine-3-carboxylic acid (301 mg, 0.78 mmol) were reacted to generate the title product (444 mg, 0.75 mmol, 93% yield) .

$^1$H NMR (CDCl$_3$): 8.34 (s, 1HO 8.01 (d, J=13.5 Hz, 1H), 7.39 (m, 1H), 7.03 (m, 2H), 4.78 (d, J=7.0 Hz, 1H), 4.31 (q, J=7.1 Hz, 2H), 4.05 (m, 1H), 3.40 (t, J=5.3 hz, 2H), 3.34 (t, J=5.3 Hz, 2H), 2.23 (t, J=10.0 Hz, 2H), 1.60–1.43 (m, 6H), 1.38 (s, 9H), 1.33 (t, J=7.1 Hz 3H).

B.
7-(2-Amino-7-azaspiro[3.5]non-7-yl)-6-fluoro-1(2,4-difluorophenyl)-1,4-dihydro-4-oxo-1,8-naphthyridine-3-carboxylic acid, hydrochloride salt A solution of 7- (2-tert-butoxycarbonylamino-7-azaspiro[3.5 ]non-7-yl) 6-fluoro-1-(2,4-difluorophenyl)-1,4-dihydro-4-oxo-1,8-naphthyridine-3-carboxylic acid, ethyl ester (399 mg, 0.68 mmol) was hydrolyzed with hydrochloric acid to provide the title product, mp 270° C. (decomp.), 223 mg (0.45 mmol, 58% yield for two steps).

$^1$H NMR (DMSO-d$_6$): 8.34 (s, 1H), 8.24 (bs, 2H), 8.09 (d, J=13.5 Hz, 1H), 7.80 (m, 1H), 7.61 (m, 1H), 3.64 (m, 1H), 3.42 (m, 4H), 2.10 (m, 2H), 1.91 (t, J=1.9 Hz, 2H), 1.52 (m, 4H).

EXAMPLE 6

A.
7-(cis-1-tert-Butoxycarbonylamino-5-azaspiro[2.5]oct-5-yl)-1-cyclopropyl-6-fluoro-1,4-dihydro-4-oxo-1,8-naphthyridine-3-carboxylic acid, ethyl ester According to the procedure of example 1A, cis-1-tert-butoxycarbonylamino-5-azaspiro[2.5]octane (125 mg, 0.47 mmol) and the ethyl ester of 7-chloro-1-cyclopropyl-6-fluoro-1,4-dihydro-4-oxo-1,8-naphthyridine-3-carboxylic acid (147 mg, 0.47 mmol) were reacted to generate the title product (255 mg, crude).

$^1$H NMR (CDCl$_3$): 8.44 (s, 1H), 8.01 (d, J=14.0 Hz, 1H), 5.00 (bs, 1H), 4.33 (q, J=7.2 Hz, 2H), 3.95 (d, J=3.7 Hz, 2H), 3.68 (d, J=3.7 Hz, 2H), 3.52 (m, 1H), 2.43 (m, 1H), 1.78 (m, 2H), 1.53 (m, 2H), 1.36 (t, J=7.2 Hz, 3H), 1.29 (s, 9H), 1.14 (d, J=7.2 Hz, 3H), 0.99 (m, 1H), 0.91 (m, 1H), 0.76 (t, J=4.1 Hz, 1H), 0.55 (m, 1H).

B.
7-(cis-1-Amino-5-azaspiro[2.5]oct-5-yl)-1-cyclopropyl-6-fluoro-1,4-dihydro-4-oxo-1,8-naphthyridine-3-carboxylic acid, hydrochloride salt According to the procedure of example 1B, the compound of step A (230 mg, 0.45 mmol) was hydrolyzed with hydrochloric acid to provide the title product, mp 236° C. (decomp.), 73.5 mg (0.18 mmol, 38% yield).

$^1$H NMR (DMSO-d$_6$): 8.59 (s, 1H), 8.56 (bs, 2H), 8.06 (d, J=13.6 Hz, 1H), 3.97–3.80 (m, 4H), 2.46 (m, 1H), 1.77 (m, 2H), 1.59 (m, 1H), 1.46 (m, 1H), 1.20–1.10 (m, 4H), 1.01 (m, 2H), 0.80 (t, J=7.2 Hz, 1H).

EXAMPLE 7

A.
7-(cis-1-tert-Butoxycarbonylamino-5-azaspiro[2.5]oct-5-yl)-6-fluoro-1-(2,4-difluorophenyl)-1,4-dihydro-4-oxo-1,8-naphthyridine-3-carboxylic acid, ethyl ester According to the procedure of example 1A, cis-1-tert-butoxycarbonylamino-5-azaspiro[2.5]octane (190 mg, 0.84 mmol) and the ethyl ester of 7-chloro-6-fluoro-1-(2,4difluorophenyl)-1,4-dihydro-4-oxo-1,8-naphthyridine-3-carboxylic acid (289 mg, 0.76 mmol) were reacted to generate the title product (293 mg, 0.51 mmol, 68% yield).

$^1$H NMR (CDCl$_3$): 8.33 (s, 1H), 8.02 (d, J=14.2 Hz, 1H), 7.42 (m, 1H), 7.05 (m, 2H), 4.46 (s, 1H), 4.33 (q, J=7.0 Hz, 2H), 3.63 (m, 2H), 3.46 (m, 2H), 2.31 (bs, 1H), 1.66 (m, 2H), 1.61 (m, 2H), 1.57 (t, J=7.0 Hz, 3H), 1.37 (s, 9H), 0.59 (m, 1H), 0.25 (m, 1H).

B.
7-(cis-1-Amino-5-azaspiro[2.5]oct-5-yl)-6-fluoro-1-(2,4-difluorophenyl)1,4-dihydro-4-oxo-1,8-naphthyridine-3-carboxylic acid, hydrochloride salt According to the procedure of example 1B, the compound of step A (293 mg, 0.51 mmol) was hydrolyzed with hydrochloric acid to provide the title product, mp 192° C. (decomp.), 163 mg (0.33 mmol, 66% yield).

$^1$H NMR (DMSO-d$_6$): 8.88 (s, 1H), 8.65 (bs, 2H), 8.14 (d, J=13.9 Hz, 1H), 7.86 (m, 1H), 7.62 (t, J=8.7 Hz, 1H), 7.36 (m, 1H), 3.76 (d, J=15.8 Hz, 1H), 3.68 (d, J=15.8 Hz, 1H), 3.53 (m, 1H), 3.24 (m, 1H), 2.39 (m, 1H), 1.64 (m, 1H), 1.50 (m, 2H), 0.85 (t, J=4.8 Hz, 1H), 0.73 (m, 1H).

EXAMPLE 8

A.
7-(1-tert-Butoxycarbonylamino-6-azaspiro[2.5]oct-6-yl)-1-cyclopropyl-6,8-difluoro-1,4-dihydro-4-oxo-quinoline-3-carboxylic acid According to the procedure of example 1A, 1-tert-butoxycarbonylamino-6-azaspiro[2.5]octane (181.2 mg, 0.80 mmol) and 1-cyclopropyl-6,7,8-trifluoro-1,4-dihydro-4-oxo-quinoline-3-carboxylic acid (239.8 mg, 0.72 mmol) were reacted to generate the title product (352.2 mg, crude).

$^1$H NMR (CDCl$_3$): 8.74 (s, 1H), 7.9 (d, J=7.86 Hz, 1H), 4.80 (bs, 1H), 4.05 (m, 1H), 3.50 (m, 2H), 3.41 (m, 2H), 2.53 (m, 1H), 1.72 (m, 1H), 1.70 (m, 1H), 1.60 (m, 1H), 1.42 (s, 1H), 1.31 (m, 2H), 1.21 (m, 2H), 0.81 (t, J=6.8 Hz, 1H), 0.41 (m, 1H).

B.
7-(1-Amino-6-azaspiro[2,5]oct-6-yl)-1-cyclopropyl-6, 8-difluoro-1,4,-dihydro-4-oxo-quinoline-3-carboxylic acid, hydrochloride salt According to the procedure of example 1B, the compound of step A (352.2 mg, crude) was hydrolyzed with hydrochloric acid to provide the title product, mp 241° C. (decomp.), 130.7 mg (0.31 mmol, 43% yield for two steps).

$^1$H NMR (DMSO-d$_6$): 8.66 (s, 1H), 8.52 (bs, 2H), 7.80 (d, J=11.4 Hz, 1H), 4.12 (m, 1H), 3.51 (m, 1H), 3.32 (m, 3H), 2.46 (m, 1H), 1.87 (m, 1H), 1.77 (m, 1H), 1.57 (m, 1H), 1.43 (m, 1H), 1.20 (m, 4H), 0.83 (m, 2H).

EXAMPLE 9

A.
7-(trans-1-tert-Butoxycarbonylamino-5-azaspiro[2.5]oct-5-yl)-6-fluoro-1-(2,4-difluorophenyl)-1,4-dihydro-4-oxo-1,8-naphthyridine-3-carboxylic acid, ethyl ester According to the procedure of example 1A, trans-1-tert-butoxycarbonylamino-5-azaspiro[2.5]octane (186 mg, 0.70 mmol) and the ethyl ester of 7-chloro-6-fluoro-1-(2,4-difluorophenyl)-1,4-dihydro-4-oxo-1,8-naphthyridine-3-carboxylic acid (252.4 mg, 0. 66 mmol) were reacted to generate the title product (343.4 mg, 0.60 mmol, yield 91%).

$^1$H (CDCl$_3$): 8.34 (s, 1H), 8.03 (d, J=13.8 Hz, 1H), 7.35 (m, 1H), 7.04 (m, 2H), 4.52 (bs, 1H), 4.34 (q, J=4.34 Hz, 2H), 3.81 (m, 1H), 3.34 (m, 1H), 3.29 (m, 3H), 2.25 (m, 1H), 1.68 (m, 2H), 1.58 (m, 2H), 1.38 (s, 9H), 1.33 (t, J=4.3 Hz, 3H), 0.58 (two multiplets, 1H), 0.22 (m, 1H).

B.
7-(trans-1-Amino-5-azaspiro[2.5]oct-5-yl)-6-fluoro-1-(2,4-difluorophenyl)-1,4-dihydro-4-oxo-1,8-naphthyridine-3-carboxylic acid, hydrochloride salt According to the procedure of example 1B, the compound of step A (268.7 mg, 0.46 mmol) was hydrolyzed with hydrochloric acid to provide the title product, mp 204° C. (decomp.), 137.1 mg (0.29 mmol, 62% yield).

$^1$H NMR (D$_2$O): 8.80 (s, 1H), 7.65 (d, J=11.5 Hz, 1H), 7.58 (m, 1H), 7.30 (m, 2H), 3.76 (m, 2H), 3.42 (bs, 2H), 2.36 (m, 1H), 2.25 (m, 1H), 1.77 (m, 4H), 0.71 (m, 2H).

EXAMPLE 10

A.
7-(trans-1-tert-Butoxycarbonylamino-5-azaspiro[2.5]oct-5 yl)-1-cyclopropyl-6-fluoro-1,4-dihydro-4-oxo-quinoline-3-carboxylic acid According to the procedure of example 1A, trans-1-tert-butoxycarbonylamino-5-azaspiro[2.5]octane (150 mg, 0.66 mmol) and 1-cyclopropyl-6,7-difluoro-1,4-dihydro-4-oxo-1,8-quinoline-3-carboxylic acid (156 mg, 0.59 mmol) were reacted to generate the title product (310 mg, crude).

$^1$H NMR (CDCl$_3$): 8.63 (s, 1H), 7.81 (d, J=13.2 Hz, 1H), 4.76 (bs, 1H), 3.52 (m, 1H), 3.43 (m, 1H), 3.19 (m, 2H), 2.94 (m, 1H), 2.55 (m, 1H), 1.89 (m, 2H), 1.72 (m, 1H), 1.56 (m, 1H), 1.40 (s, 9H), 1.34 (m, 2H), 1.15 (m, 2H), 0.90 (m, 1H) 0.45 (m, 1H).

B. 7-(trans-1-Amino-5-azaspiro[2.5]oct-5-yl)-1-cyclopropyl-6-fluoro-1,4-dihydro-4-oxo-quinoline-3-carboxylic acid, hydrochloride salt According to the procedure of example 1B, the compound of step A (310 mg, crude) was hydrolyzed with hydrochloric acid to provide the title product, mp 190° C. (decomp.), 107.6 mg (0.26 mmol, 45% yield for two steps).

$^1$H NMR (DMSO-d$_6$): 8.64 (s, 1H), 8.56 (bs, 2H), 7.87 (d, J=13.1 Hz, 1H), 7.52 (d, J=7.65 Hz, 1H), 3.83 (m, 1H), 3.45 (m, 2H), 3.07 (bs, 2H), 2.58 (m, 2H), 1.94 (m, 1H), 1.80 (m, 2H), 1.30 (m, 2H), 1.18 (m, 2H), 0.92 (m, 1H), 0.82 (m, 1H).

EXAMPLE 11

A.
7-(trans-1-tert-Butoxycarbonylamino-5-azaspiro[2.5]oct-5-yl)-1-cyclopropyl-6,8-difluoro-1,4-dihydro-4-oxo-quinoline-3-carboxylic acid According to the procedure of example 1A, trans-1-tert-butoxycarbonylamino-5-azaspiro[2.5]octane (150 mg, 0.66 mmol) and 1-cyclopropyl-6,7,8-trifluoro-1,4-dihydro-4-oxo-quinoline-3-carboxylic acid (198 mg, 0.59 mmol) were reacted to generate the title product (347.5 mg, crude).

$^1$H NMR (CDCl$_3$): 8.78 (s, 1H), 7.74 (d, J=10.3 Hz, 1H), 4.73 (bs, 1H), 3.97 (m, 1H), 3.36 (m, 2H), 3.25 (m, 1H), 2.88 (d, J=12.5 Hz, 1H), 2.51 (m, 1H), 1.79 (m, 2H), 1.70 (m, 1H), 1.61 (m, 1H), 1.41 (s, 9H), 1.25 (m, 2H), 1.13 (m, 2H), 0.89 (m, 1H), 0.43 (m, 1H).

B.
7-(trans-1-Amino-5-azaspiro[2.5]oct-5-yl)-1-cyclopropyl-6,8,-difluoro-1,4-dihydro-4-oxo-quinoline-3-carboxylic acid, hydrochloride salt According to the procedure of example 1B, the compound of step A (347.5 mg, crude) was hydrolyzed with hydrochloric acid to provide the title product, mp 204° C. (decomp.), 145.4 mg (0.34 mmol, 58% yield for two steps).

$^1$H NMR (DMSO-d$_6$): 8.66 (s, 1H), 8.45 (bs, 2H), 7.80 (d, J=11.9 Hz, 1H), 4.11 (m, 1H), 3.47 (m, 1H), 3.41 (m, 1H), 3.14 (d, J-12.2 Hz, 1H), 3.02 (d, J=12.2 Hz, 1H), 2.56 (m, 1H), 1.90–1.75 (m, 4H), 1.19 (m, 4H), 0.91 (m, 1H), 0.77 (m, 1H).

EXAMPLE 12

A.
7-(2-tert-Butoxycarbonylamino-7-azaspiro[3.5]non-7-yl)-1-cyclopropyl-6-fluoro-1,4-dihydro-4-oxo-1,8-naphthyridine-3-carboxylic acid, ethyl ester According to the procedure of example 1A, 2-tert-butoxycarbonylamino-7-azaspiro[3.5]nonane (200 mg, 0.83 mmol) and the ethyl ester of 7-chloro-1-cyclopropyl-6-fluoro-1,4-dihydro-4-oxo-1,8 -naphthyridine-3-carboxylic acid (242 mg, 0.78 mmol) were reacted to generate the title product (405 mg, 0.78 mmol, yield 100%, crude).

$^1$H NMR (CDCl$_3$): 8.38 (s, 1H), 7.94 (d, J=13.6 Hz, 1H), 4.92 (d, J=7.1 Hz, 1H), 4.28 (q, J=7.1 Hz, 2H), 4.08 (m, 1H), 3.67 (t, J=5.3 Hz, 2H), 3.60 (t, J=5.3 Hz, 2H), 3.42 (m, 1H), 2.28 (t, J=10.1 Hz, 2H), 1.66–1.59 (m, 6H), 1.35 (s, 9H), 1.31 (t, J=7.1 Hz, 3H), 1.12 (m, 2H), 0.94 (m, 2H).

B.
7-(Amino-7-azaspiro[3.5]non-7-yl)-1-cyclopropyl-6-fluoro-1,4-dihydro-4-oxo-1,8-naphthyridine-3-carboxylic acid, hydrochloride salt According to the procedure of example 1B, the compound of step A (288 mg, 0.56 mmol) was hydrolyzed with hydrochloric acid to provide the title product, mp 213°–215° C. (decomp.), 134 mg (0.29 mmol, 58% yield for two steps).

$^1$H NMR (D$_2$O): 8.48 (s, 1H), 7.37 (d, J=7.4 Hz, 1H), 3.91 (m, 1H), 3.80 (m, 2H), 3.73 (m, 2H), 3.53 (m, 1H), 2.42 (m, 2H), 2.04 (m, 2H), 1.77 (m, 4H), 1.26 (d, J=7.1 Hz, 2H), 0.98 (m, 2H).

Preparation A

1. 1-Benzyloxycarbonyl-4-piperidone

A mixture of 4-piperidone monohydrate hydrochloride (15 g, 0.10 mol), benzyl chloroformate (17 ml, 0.12 mol) and sodium bicarbonate (25 g, 0.50 mol in dioxane (120 ml) and water (100 ml) was stirred at room temperature for 48 hours. Water was added and the mixture was extracted with methylene chloride; the organic layer was washed with brine and dried over magnesium sulfate. Upon evaporation, the title compound was obtained as a colorless liquid (21.7 g, 0.093 mol, yield 93%)

$^1$H NMR (CDCl$_3$): 7.36 (m, 5H), 5.15 (s, 2H), 3.78 (t, J=6.3 Hz, 4H), 2.43 (m, 4H).

2. 1-Benzyloxycarbonyl-4-methylenepiperidine

In a flame-dried, 500-ml three-necked flask containing a condenser was placed sodium hydride (2.42 g of a 60% suspension in oil, 66.7 mmol), which was washed with pentane twice (50 ml each time). 120 ml of dry dimethyl sulfoxide was added and the suspension was warmed to 65° C. for 1.5 hours. The resulting grey clear solution was cooled to 0° C. and a solution of methyltriphenylphosphoniumbromide (23.58 g, 66.2 mmol) in dimethyl sulfoxide (140 ml) was added. The mixture was stirred at room temperature for 45 minutes; the title compound of step I (12.85 g, 55.2 mmol) was slowly added. The reaction mixture was heated at 50° C. for 1.5 hours. Water was added and the mixture was extracted with ether. The ether layer was washed several times with brine and dried over magnesium sulfate. Evaporation in vacuo afforded a yellow oil which was purified by chromatography on silica gel (eluent: 10% ethyl acetate/hexane) to give the title compound as a colorless liquid (11.15 g, 48.2 mmol, yield 88% ).

$^1$H NMR (CDCl$_3$): 7.35 (m, 5H), 5.13 (s, 2H), 4.74 (s, 2H), 3.49 (t, J=5.5 Hz, 4H), 2.18 (m, 4H).

3. 6-Benzyloxycarbonyl-6,azaspiro[2.5]octane-1-carboxylic acid, ethyl ester

A solution of the title compound of step 2 (5.0 g, 21.63 mmol) in methylene chloride (250 ml) was treated with rhodium acetate (285 mg, 1.29 mmol). A solution of ethyl diazoacetate (6.81 ml, 64.89 mmol) in methylene chloride (3.2 ml) was then added over 20 hours (at the rate of 0.5 ml/hr), via a syringe pump. After completion of the addition, the reaction mixture was filtered through celite; concentration of the filtrate provided the crude product mixture. This was then chromatographed on silica gel (eluent: 15% ethyl acetate/hexane) to give 3.35 g (10.5 mmol, yield 49%) of the pure title compound as a yellow viscous oil and another portion of 1.19 g containing 60% (by NMR) of the product (yield 16.5% ).

$^1$H NMR (CDCl$_3$): 7.30 (m, 5H), 5.10 (s, 2H), 4.10 (q, J=7.2 Hz, 2H), 3.50 (m, 3H), 3.32 (m, 1H), 1.69 (m, 2H), 1.53 (dd, J=8.4, 5.1 Hz, 1H), 1.39 (m, 2H), 1.23 (t, J=7.2 Hz, 3H), 1.14 (t, J=5.0 Hz, 1H), 0.89 (dd, J=8.4, 3.8 Hz, 1H).

4. 6-Benzyloxycarbonyl-6-azaspiro[2.5]octane-1carboxylic acid

The title compound of step 3 (2.85 g, 8.98 mmol) was dissolved in aqueous dioxane (20% by volume, 180 ml). Powdered sodium hydroxide (3.59 g) was added and the mixture was stirred at 60° C. for 2 hours. After being cooled to room temperature, the solution was extracted with ether. The aqueous layer was acidified with sodium bisulfate to a pH of 2 and extracted with methylene chloride. The methylene chloride layers were washed with brine, dried over magnesium sulfate and concentrated to afford the title compound (2.28 g, 7.90 mmol, yield 88%).

$^1$H NMR (CDCl$_3$): 7.33 (m, 3H), 7.16 (m, 2H), 5.11 (s, 2H), 3.53 (m, 3H), 3.43 (m, 1H), 1.74 (m, 2H), 1.57 (dd, J=8.0, 5.0, 1H), 1.43 (m, 2H), 1.19 (t, J=4.9, 1H), 1.00 (m, 1H).

5. 6-Benzyloxycarbonyl-1-(tert-butoxycarbonyl)amino-6-azaspiro[2.5]octane

A mixture of the title compound of step 4 (2.28 g, 7.88 mmol) and triethylamine (1.2 ml, 8.66 mmol) in acetone (80 ml) was cooled to 0° C.; ethyl chloroformate (0.90 ml, 9.45 mmol) was added dropwise. The mixture was stirred at 0° C. for 30 minutes. A solution of sodium azide (5.12 g, 78.8 mmol) in water (10 ml) was then added slowly. After an additional 2 hours, the mixture was diluted with water and extracted with ether. The ether layer was washed with brine, dried over magnesium sulfate and concentrated in vacuo to give the acyl azide (2.45 g, 7.78 mmol, crude) which was used directly in the next reaction.

A solution of the acyl azide in toluene (100 ml) was added dropwise into a toluene solution (150 ml) of t-butanol (40 ml) and pyridinium tosylate (10 mg) at 100° C. After completion of the addition, the reaction mixture was maintained at 100° C. for 12 hours. The reaction mixture was concentrated in vacuo, and the residue was chromatographed on silica gel (eluent: 22% ethyl acetate/hexane), providing the title compound as a colorless foam (2.26 g 6.28 mmol, 80% yield).

$^1$H NMR (CDCl$_3$): 7.32 (m, 5H), 5.11 (s, 2H), 4.61 (bs, 1H), 3.56 (bm, 4H), 2.42 (m, 1H), 1.41 (s, 9H), 1.34 (m, 4H), 0.72 (dd, J=7.6, 6.0 Hz, 1H), 0.31 (m, 1H).

6. 1-(tert-Butoxycarbonyl)amino-6-azaspiro[2.5]octane

To a solution of the title compound of step 5 (2.2 g, 6.10 mmol) in ethanol (60 ml) was added ammonium formate (1.15 g, 18.3 mmol) followed by palladium on activated carbon (10% palladium content, 1.94 g, 1.83 mmol). The mixture was stirred at room temperature for 1 hour. The reaction mixture was filtered, and the filtrate was concentrated in vacuo to afford the title compound as a white foam (1.4 g, 6.1 mmol, yield 100%).

$^1$H NMR (CD$_3$OD): 8.54 (s, 1H), 3.30 (m, 1H), 3.04 (m, 3H), 2.39 (m, 1H), 1.60 (m, 1H), 1.50 (m, 4H), 1.44 (s, 9H), 0.75 (t, J=7.2 Hz, 1H), 0.46 (m, 1H).

Preparation B

1. 1-Benzyloxycarbonyl-3-hydroxypiperidine

To a solution of 3-hydroxypiperidine hydrochloride (20.0 g, 0.145 mol) in dioxane (500 ml) and water (500 ml) was added benzyl chloroformate (24.88 ml, 0.17 mol) and triethylamine (101 ml, 0.73 mol). The mixture was stirred at room temperature overnight. The reaction mixture was extracted with ether and the organic layer was washed with brine, dried over magnesium sulfate and concentrated. The crude product was purified through chromatography on silica gel (eluent: 1:1 ethyl acetate/hexane) and the title compound was obtained as a pale yellow viscous oil (20.7 g, 88 mmol, yield 61%).

$^1$H NMR (CDCl$_3$): 7.33 (m, 5H), 5.09 (s, 2H), 3.78 (dd, J=13, 3.5 Hz, 1H), 3.69 (m, 1H), 3.58 (m, 1H), 3.16 (m, 1H), 3.08 (dd, J=13, 7.3 Hz, 1H), 1.85 (m, 1H), 1.75 (m, 1H), 1.47 (m, 2H).

2. 1-Benzyloxycarbonyl-3-piperidone

To a solution of the title compound of step 1 (10.6 g, 45 mmol) in acetone (500 ml) was added Jones reagent (17.0 ml) dropwise at 0° C. The mixture was stirred at this temperature for 2 hours. After being diluted with water, the product was extracted into methylene chloride and the combined organic layers were washed with brine and dried over magnesium sulfate. Removal of solvent in vacuo provided the title compound as a pale yellow, viscous oil (10.4 g, 44.4 mmol, yield 98.5%).

$^1$H NMR (CDCl$_3$): 7.32 (m, 5H), 5.11 (s, 2H), 4.04 (s, 2H), 3.62 (t, J=5.8 Hz, 2H), 2.43 (t, J=6.8 Hz, 2H), 1.95 (m, 2H).

3. 1-Benzyloxycarbonyl-3-methylene-piperidine

In a flame-dried, three-necked flask, equipped with a condenser and an addition funnel, was placed sodium hydride (1.95 g of a 60% suspension in oil, 48.9 mmol) which was washed with pentans twice (20 ml each time). 100 ml of dry dimethyl sulfoxide was added and the suspension was warmed to 65° C. for 1.5 hours. The resulting grey, clear solution was cooled to room temperature and a solution of methyltriphenylphosphonium bromide (19.1 g, 53.4 mmol) in dimethyl sulfoxide (150 ml) was added through the addition funnel. The bright yellow solution was stirred at room temperature for 45 minutes; the title compound of step 2 (10.38 g, 44.5 mmol) was slowly added. The reaction mixture was heated at 50° C. for 5.5 hours. Water was added and the mixture was extracted with ether. The ether layer was washed several times with brine and dried over magnesium sulfate. Evaporation in vacuo afforded a yellow oil which was purified by chromatography on silica gel (eluent: 15% ethyl acetate/hexane) to give the title compound as a colorless liquid (3.12 g, 13.5 mmol, yield 30.3%).

$^1$H NMR (CDCl$_3$): 7.31 (m, 5H), 5.11 (s, 2H), 4.82 (bs, 1H), 4.75 (s, 1H), 3.94 (s, 2H), 3.50 (t, J=6 Hz, 2H), 2.25 (t, J=6 Hz, 2H), 1.61 (m, 2H).

4. trans-5-Benzyloxycarbonyl-5-azaspiro[2,5]octane-1-carboxylic acid, ethyl ester A solution of the title compound of step 3 (4.25 g, 18.3 mmol) in methylene chloride (180 ml) was treated with rhodium acetate (242 mg, 1.1 mmol). The ethyl diazoacetate (5.76 ml, 54.9 mmol) was added over 23 hours via syringe pump. After completion of the addition, the reaction mixture was filtered through celite; concentration of the filtrate provided the crude product mixture. The mixture was chromatographed on silica gel (eluent: 15% ethyl acetate/hexane) to afford 2.44 g (7.70 mmol, yield 42%) of the title compound from the fraction with high R$_f$ value (R$_f$ 0.44, 15% ethyl acetate/hexane). The fraction with low R$_f$ value (R$_f$ 0.34, 15% ethyl acetate/hexane) provided the cis isomer (1.05 g 3.31 mmol, yield 18%).

$^1$H NMR for title compound (CDCl$_3$): 7.32 (m, 5H), 5.10 (s, 2H), 4.08 (q, J=6.8 Hz, 3H), 3.47 (bm, 2H), 3.24 (bm, 2H), 1.75 (m, 2H), 1.59 (bm, 2H), 1.49 (m, 2H), 1.23 (t, J=6.8 Hz, 2H), 1.07 (t, 4.6 Hz, 1H).

$^1$H NMR for the cis isomer (CDCl$_3$): 7.32 (m, 5H), 5.09 (d, J=12 Hz, 1H), 5.05 (d, J=12 Hz, 1H), 4.20 (q, J=7.0 Hz, 2H), 4.15 (bm, 2H), 3.60–3.50 (bin, 4H), 1.63 (m, 2H), 1.45 (m, 2H), 1.25 (t, J=7.0 Hz), 1.16 (bm, 1H), 0.81 (dd, J=8.0, 4.7 Hz, 1H).

5. trans-5-Benzyloxycarbonyl-5-azaspiro[2.5]octane-1-carboxylic acid

The title compound of step 4 (2.40 g, 7.51 mmol) was dissolved in aqueous dioxane (20% by volume, 100 ml). Powdered sodium hydroxide (3.0 g, 75 mmol) was added, and the mixture was stirred at 60° C. for 2 hours. After being cooled to room temperature, the solution was extracted with methylene chloride. The aqueous layer was then acidified with sodium bisulfate to a pH of 2 and extracted with ether. The ether layers were then washed with brine, dried over magnesium sulfate and concentrated to afford the title compound (1.38 g, 4.78 mmol, yield 63%).

$^1$H NMR (CDCl$_3$): 7.30 (m, 5H), 5.09 (s, 2H) 3.54 (bm, 1H), 3.44 (m, 1H), 3.24 (bm, 2H), 1.78 (m, 2H), 1.70 (m, 1H), 1.57 (bm, 2H), 1.10 (m, 2H).

6. trans-5-Benzyloxycarbonyl-1-(tert-butoxycarbonyl)-amino-5-azaspiro[2.5]octane-1-carboxylic acid A mixture of the title compound of step 5 (1.38 g, 4.7 mmol) and triethylamine (0.72 ml, 5.1 mmol) in acetone (100 ml) was cooled to 0° C. and ethyl chloroformate (0.53 ml, 5.6 mmol) was added dropwise. The mixture was stirred at 0° C. for 30 minutes. A solution of sodium azide (3.05 g, 47.0 mmol) in water (10 ml) was then added slowly. After an additional 2 hours, the mixture was diluted with water and extracted with ether. The ether layer was washed with brine, dried over magnesium sulfate and concentrated in vacuo to give the acyl azide (1.07 g, 3.4 mmol, crude), which was used directly in the next reaction.

A solution of the acyl azide in toluene (30 ml) was added dropwise into a toluene solution (20 ml) of t-butanol (25 ml) and pyridinium rosylate (10 mg) at 100° C. After completion of the addition, the reaction mixture was maintained at 100° C. for 24 hours. The reaction mixture was concentrated in vacuo and the residue was purified on a chromatotron (eluent: 11% ethyl acetate/hexane), providing the title compound as a pale yellow, viscous oil (0.92 g, 2.6 mmol, yield 54.3% ).

$^1$H NMR (CDCl$_3$): 7.30 (m, 5H), 5.08 (bs, 2H), 4.62 (bm, 1H), 3.65 (bm, 1H), 3.21 (bm, 3H), 2.45 (bm, 1H), 1.93 (bm, 1H), 1.61 (bm, 3H), 1.36 (bs, 9H), 0.82 (bm, 1H), 0.28 (bm, 1H).

7. trans-1-(tert-Butoxycarbonyl) amino-5-azaspiro[2.5-octane hydrochloride

To a solution of the title compound of step 6 (0.92 g, 2.55 mmol) in ethanol (50 ml) was added ammonium formate (482 mg, 7.65 mmol) followed by palladium on activated carbon (10% palladium content, 811 mg, 0.76 mmol). The mixture was stirred at room temperature for 2.5 hours. The reaction mixture was filtered, and the filtrate was concentrated in vacuo. The crude product was dissolved in acetone (10 ml) and an ether solution (2.5 ml, 1.0 M) of hydrogen chloride was added. The resulting suspension was concentrated and the residue was triturated with ether to form the hydrochloride salt precipitate. After filtration, the title compound was obtained as a white solid (426 mg, 1.61 mmol, yield 63%).

¹H NMR (CDCl₃): 4.85 (bs, 1H), 3.17–2.90 (bm, 5H), 2.59 (bm, 1H), 1.91 (bm, 2H), 1.63 (bm, 1H), 1.55 (bm, 1H), 1.39 (s, 9H), 1.13 (bm, 1H), 0.64 (bm, 1H).

Preparation C

1. cis-5-Benzyloxycarbonyl-5-azaspiro[2.5]octane-1-carboxylic acid.

Cis-5-Benzyloxycarbonyl-5-azaspiro[2.5]octane-1-carboxylic acid, ethyl ester, (1.05 g, 3.3 mmol) was dissolved in aqueous dioxane (20% by volume, 100 ml). Powdered sodium hydroxide (1.32 g, 3.3 mmol) was added, and the mixture was stirred at 60° C. for 2 hours. After being cooled to room temperature, the solution was extracted with methylene chloride. The aqueous layer was acidified with sodium bisulfate to a pH of 2 and extracted with ether. The ether layers were washed with brine, dried over magnesium sulfate and concentrated to afford the title compound (730 mg, 2.5 mmol, yield 76.5%).

¹H NMR (CDCl₃): 9.99 (bs, 1H), 7.31 (m, 5H), 5.02 (bm, 2H), 3.71 (bm, 1H), 3.45 (bm, 3H), 1.63 (bm, 2H), 1.51 (m, 3H), 1.24 (bm, 1H), 0.87 (dd, J=7.6, 4.6 Hz, 1H).

2. cis-5-Benzyloxycarbonyl-1-(tert-butoxycarbonyl)-amino-5-azaspiro[2.5]octane A mixture of the title compound of step 1 (0.73 g, 2.53 mmol) and triethylamine (0.38 ml, 2.75 mmol) in acetone (25 ml) was cooled to 0° C.; ethyl chloroformate (0.29 ml, 2.99 mmol) was added dropwise. The mixture was stirred at 0° C. for 30 minutes. A solution of sodium azide (1.62 g, 25 mmol) in water (5 ml) was added slowly. After an additional 2 hours, the mixture was diluted with water and extracted with ether. The ether layer was washed with brine, dried over magnesium sulfate and concentrated in vacuo to give the acyl azide (0.74 g, 2.36 mmol, crude) which was used directly in the next reaction.

A solution of the acyl azide in toluene (50 ml) was added dropwise into a toluene solution (50 ml) of t-butanol (30 ml) and pyridinium tosylate (10 mg) at 100° C. After completion of the addition, the reaction mixture was maintained at 100° C. for 24 hours. The reaction mixture was concentrated in vacuo, and the residue was purified on a chromatotron (eluent: 11% ethyl acetate/hexane), providing the title compound as a yellow foam (0.72 g, 1.99 mmol, yield 79%).

¹H NMR (CDCl₃): 7.34 (m, 5H), 5.12 (s, 2H), 3.74 (bm, 1H), 3.52 (bm, 1H), 3.30 (bm, 2H), 2.34 (bm, 1H), 1.57 (bm, 2H), 1.49 (m, 2H), 1.43 (s, 9H), 1.23 (m, 1H), 0.73 (m, 1H), 0.53 (m, 1H).

3. cis-1-(tert-Butoxycarbonyl)amino-5-azaspiro[2,5]octane

To a solution of the title compound of step 2 (0.72 g, 1.99 mmol) in ethanol (50 ml) was added ammonium formate (376 mg, 5.97 mmol) followed by palladium on activated carbon (10% palladium content, 625.6 mg, 0.59 mmol). The mixture was stirred at room temperature for 2.5 hours. The reaction mixture was filtered, and the filtrate was concentrated in vacuo to afford the title compound as a white foam (220 mg, 0.97 mmol, yield 49%).

¹H NMR (CDCl₃): 5.87 (bs, 1H), 3.38 (m, 1H), 3.22 (m, 1H), 2.97 (m, 2H), 2.37 (m, 1H), 2.03 (m, 1H), 1.86 (bm, 2H), 1.41 (s, 9H), 1.13 (m, 1H), 0.86 (m, 2H), 0.67 (dd, J=6.6, 4.2 Hz, 1H).

Preparation D

1. 7-Benzyloxycarbonyl-1,1-dichloro-7-azaspiro[3.5]-nonan-3-one

To a stirred solution of 1-benzyloxycarbonyl-4-methylenepiperidine (11.1 g, 49.3 mmol) and zinc-copper couple (95: 5, 7.98 g, 12.2 mmol) in 200 ml of anhydrous ether was added a solution of trichloroacetyl chloride (10.18 ml, 91.2 mmol) and phosphorous oxychloride (8.77 ml, 94.0 mmol) in 50 ml of anhydrous ether. The reaction mixture was refluxed overnight. After cooling to room temperature, the solution was filtered through celite and the filtrate was washed with brine and cold sodium bicarbonate, dried over magnesium sulfate and upon evaporation afforded the title compound as a yellow liquid, 15.3 g (crude).

¹H NMR (CDCl₃): 7.36–7.24 (m, 5H), 5.12 (s, 2H), 4.15 (bm, 2H), 3.08 (s, 2H), 2.95 (m, 2H), 1.92 (m, 2H), 1.1.74 (m, 2H).

2. 7-Benzyloxycarbonyl-7-azaspiro[3.5]nonan-3-one

To a stirred mixture of the title compound of Preparation D.1 (15.3 g) and ammonium chloride (7.16 g, 134 mmol) in methanol (200 ml) was added zinc dust (8.76 g, 134 mmol). The mixture was refluxed for 5 hours. After cooling to room temperature, the solution was filtered through celite, and the solvent was removed in vacuo. The resulting oil was dissolved in methylene chloride and washed with brine, cold saturated sodium bicarbonate solution and dried over magnesium sulfate. Evaporation in vacuo afforded a yellow, viscous oil, 7.28 g (26.7 mmol, 54% yield from 1-benzyloxycarbonyl-4-methylenepiperidine).

¹H NMR (CDCl₃): 7.34 (m, 5H), 5.11 (s, 2H), 3.47 (m, 4H), 2.80 (s, 4H), 1.69 (m, 4H).

3. 7-Benzyloxycarbonyl-7-azaspiro[3.5]nonan-2-ol

To a solution of the title compound of Preparation D.2 (7.28 g, 26.7 mmol) was added sodium borohydride powder (5.07 g, 133.5 mmol) in portions at 0° C. The mixture was stirred at 0° C. for four hours. After addition of water, the mixture was extracted with ether, the organic layer was washed with brine and dried over magnesium sulfate. Evaporation in vacuo afforded the crude product which was chromatographed on silica gel (eluent: 20%, then 40% ethyl acetate/hexane), providing the pure title compound as a colorless viscous oil (5.589 g, 20.3 mmol, 76% yield).

¹H NMR (CDCl₃): 7.31 (m, 5H), 5.08 (s, 2H), 4.27 (m, 1H), 3.36 (m, 4H), 2.38 (d, J=4.6 Hz, 1H), 2.23 (m, 2H), 1.66 (m, 2H), 1.48 (bm, 4H).

4. 7-Benzyloxycarbonyl-2-azido-7-azaspiro[3.5]nonane

To a stirred solution of the title compound of Preparation D.3 (5.53 g, 20.0 mmol) in methylene chloride (60 ml) was added triethylamine (8.4 ml, 60.0 mmol) followed by addition of methanesulfonyl chloride (2.32 ml, 30.0 mmol) at 0° C. The mixture was stirred at 0° C. for three hours. After addition of water, the mixture was extracted with methylene chloride and the organic layer was washed with brine, dried over magnesium sulfate and concentrated to give 7-benzyloxycarbonyl-2-methylsulfonyloxyl-7-azaspiro[3.5]nonane as a pale yellow oil (7.47 g, crude).

To a stirred solution of the mesylate (7.39 g, 20.0 mmol, crude) in N,N-dimethylformamide (60 ml) was added sodium azide (3.9 g, 60.0 mmol) and the mixture was heated at 90° C. for four hours. The solution was cooled to room temperature and methylene chloride was added. The organic layer was washed with brine, dried over magnesium sulfate and concentrated to give the crude product which was purified through chromatography on silica gel (eluents: 30% ethyl acetate/hexane) to afford the pure title compound as a colorless oil (4.51 g, 15.0 mmol, 75% yield from the title compound of Preparation D. 3).

$^1$H NMR (CDCl$_3$): 732 (m, 5H), 5.09 (s, 2H), 3.87 (quint., J=7.7 Hz, 1H), 3.38 (m, 4H), 2.22 (m, 2H), 1.83 (m, 2H), 1.53 (bs, 4H).

5. 7-Benzyloxycarbonyl-2-amino-7-azaspiro[3.5]nonane

A solution of the title compound of Preparation D.4 (4.43 g, 14.8 mmol) in ethanol (50 ml) was stirred with Lindlar catalyst (1.92 g, 1.48 mmol, 5% Pd/CaCO3) under 1 atm of hydrogen for 4.5 hours. The solution was filtered through celite and the filtrate was concentrated in vacuo to afford the title compound as a colorless, viscous oil (3.84 g, 14.0 mmol, crude).

$^1$H NMR (CDCl$_3$): 7.28 (m, 5H), 5.05 (s, 2H), 3.38 (t, J=5.7 Hz, 2H), 3.30 (t, J=5.7 Hz, 2H), 2.17 (m, 2H), 1.52–1.34 (bm, 7H).

6. 2-(tert-Butoxycarbonyl)amino-7-azaspiro[3.5]nonane

To a solution of the title compound of Preparation D.5 (3.73 g, 13.6 mmol) and di-t-butyl dicarbonate (3.58 g, 16.3 mmol) in dioxane (50 ml) and water (5 ml) was added triethylamine (2.9 ml, 20.4 mmol). The mixture was stirred at room temperature overnight, diluted with saturated sodium bicarbonate and extracted with methylene chloride. The organic layer was washed with brine, dried over magnesium sulfate and evaporated to give a colorless viscous oil. This oil was chromatographed on silica gel (eluents: 30% ethyl acetate/hexane) to afford 7-benzyloxycarbonyl-2-(tertbutoxycarbonyl)amino-7-azaspiro[3.5]nonane (5.38 g, crude).

$^1$H NMR (CDCl$_3$): 7.29 (m, 5H), 5.06 (s, 2H), 4.74 (bs, 1H), 3.39 (m, 2H), 3.31 (m, 2H), 2.36 (m, 2H), 1.58–1.44 (bm, 4H), 1.39 (s, 9H).

To a solution of the tert-butoxycarbonylaminospirononane (5.08 g, crude) in ethanol (50 ml) was added ammonium formate (2.57 g, 40.8 mmol) followed by palladium on activated carbon (10% palladium content, 4.32 g, 4.08 mmol). The mixture was stirred at room temperature for 3 hours. The reaction mixture was filtered, and the filtrate was concentrated in vacuo to give a white foam. This foam was triturated with ether to afford the pure title compound as a white solid. (1.86 g, 7.75 mmol, 52.5% yield from the title compound of Preparation D.4.)

$^1$H NMR (CDCl$_3$): 6.23 (bs, 1H), 4.66 (d, J=7.1 Hz, 1H), 4.06 (bm, 1H), 2.98 (t, J=5.2 Hz, 2H), 2.91 (t, J=5.2 Hz, 2H), 2.28 (t, J=9.9 Hz, 2H), 1.80 (t, J=5.1 Hz, 2H), 1.73 (t, J=5.1 Hz, 2H), 1.62 (m, 2H), 1.30 (s, 9H).

I claim:

1. A compound of the formula wherein
$R^1$ is hydrogen, $C_1$–$C_3$ alkyl, benzyl, or a pharmaceutically acceptable cation,
A is CH, CF CCl, COCH$_3$, C-CH=CH$_2$, C—($C_1$–$C_3$) alkyl, C—CF$_3$, C—CN or N;
Y is $C_1$–$C_3$ alkyl, $C_1$–$C_2$ haloalkyl, cyclopropyl, halocyclopropyl, vinyl, 4-halophenyl, 2,4-difluorophenyl, methoxy or NHCH$_3$;

$$=\overset{|}{C}-X-(CH_2)_n-B-$$

$R^2$ is hydrogen, $C_1$–$C_4$ alkyl, $C_1$–$C_4$ alkoxy, amino, halogen or aminomethyl; and
$R^3$ is a group of the formula wherein $R^5$ is hydrogen or $C_1$–$C_3$ alkyl, $R^6$ and $R^7$ are each independently hydrogen, $C_1$–$C_3$ alkyl or halogen, m is 2 or 3, p is 1 or 2, q is 2 or 3 p+q is 4, and $R^6$ is located next to the group NHR$^5$.

2. A compound according to claim 1 wherein $R^1$ is hydrogen and A is CH or N.

3. A compound according to claim 1 wherein Y is cyclopropyl or 2,4-difluorophenyl.

4. A compound according to claim 1 wherein said compound is 7-(1-amino-6-azaspiro[2.5]oct-6-yl)-1-(2,4-difluorophenyl)-6-fluoro-1,4-dihydro-4-oxo-naphthyridine-3-carboxylic acid, 7-(1-amino-6-azaspiro[2.5]oct-6-yl)-1-cyclopropyl-6-fluoro-1,4-dihydro-4-oxo-quinoline-3-carboxylic acid, 7-(1-amino-6-azaspiro[2.5]oct-6-yl)-1-cyclopropyl-6-fluoro-1,4-dihydro-4-oxo-1,8-naphthyridine-3-carboxylic acid, 7-(trans-1-amino-5-azaspiro[2.5]oct-5-yl)-1-cyclopropyl-6-fluoro-1,4-dihydro-4-oxo-1,8-naphthyridine-3-carboxylic acid, or 7-(2-amino-7-azaspiro[3.5]non-7-yl)-1-(2,4-difluorophenyl)-6-fluoro-1,4-dihydro-4-oxo-1,8-naphthyridine-3-carboxylic acid.

5. A compound according to claim 1, wherein $R^3$ is 1-amino-6-azaspiro[2.5]oct-6-yl.

6. A compound according to claim 1, wherein $R^3$ is 1-amino-5-azaspiro[2.5]oct-5-yl.

7. A compound according to claim 1, wherein $R^3$ is 2-amino-7-azaspiro[3.5]non-7-yl.

8. An antibacterial composition comprising a compound according to claim 1 and a pharmaceutically acceptable carrier.

9. A method of treating a host afffected by a bacterial infection which comprises administering to said host an antibacterially effective amount of a compound according to claim 1.

* * * * *